United States Patent
Takeuchi

(10) Patent No.: US 9,050,478 B2
(45) Date of Patent: Jun. 9, 2015

(54) SUPPLY VALVE FOR AIR RESPIRATOR

(75) Inventor: Hironobu Takeuchi, Tokyo (JP)

(73) Assignee: KOKEN LTD., Tokyo (JP)

( * ) Notice: Subject to any disclaimer, the term of this patent is extended or adjusted under 35 U.S.C. 154(b) by 386 days.

(21) Appl. No.: 13/643,733

(22) PCT Filed: Apr. 26, 2011

(86) PCT No.: PCT/JP2011/060171
§ 371 (c)(1),
(2), (4) Date: Oct. 26, 2012

(87) PCT Pub. No.: WO2011/136225
PCT Pub. Date: Nov. 3, 2011

(65) Prior Publication Data
US 2013/0047991 A1     Feb. 28, 2013

(30) Foreign Application Priority Data

Apr. 28, 2010 (JP) ................... 2010-104481

(51) Int. Cl.
| | | |
|---|---|---|
| A61M 11/00 | (2006.01) |
| A62B 18/10 | (2006.01) |
| A61M 16/20 | (2006.01) |
| A62B 9/02 | (2006.01) |
| F16K 1/30 | (2006.01) |
| F16K 31/143 | (2006.01) |
| F16K 31/163 | (2006.01) |
| A61M 16/00 | (2006.01) |

(52) U.S. Cl.
CPC .............. *A62B 18/10* (2013.01); *A61M 16/20* (2013.01); *A61M 2016/0015* (2013.01); *A62B 9/02* (2013.01); *F16K 1/307* (2013.01); *F16K 31/143* (2013.01); *F16K 31/163* (2013.01); *A61M 16/201* (2014.02); *A61M 16/207* (2014.02)

(58) Field of Classification Search
CPC ........ A62B 18/045; A62B 18/08; A62B 7/02; A62B 18/02; A61M 16/0627; A61M 16/0633
USPC ........................ 128/201.23–201.29; 251/26; 137/115.07, 115.23, 490, 908, 505.46
See application file for complete search history.

(56) References Cited

U.S. PATENT DOCUMENTS

| 6,394,091 B1 * | 5/2002 | Giorgini ................... 128/206.21 |
| 7,100,628 B1 * | 9/2006 | Izenson et al. ................... 137/14 |
| 2004/0000311 A1 * | 1/2004 | Lowry ...................... 128/204.26 |

FOREIGN PATENT DOCUMENTS

| JP | 58-133363 | 9/1983 |
| JP | 58-501656 | 10/1983 |
| JP | 05-057031 | 3/1993 |
| JP | 06-107278 | 4/1994 |
| JP | 09-504854 | 5/1997 |
| JP | 2001-088782 | 4/2001 |

\* cited by examiner

*Primary Examiner* — Steven Douglas
(74) *Attorney, Agent, or Firm* — Clark & Brody

(57) ABSTRACT

A supply valve for supplying air to a wearer of an air respirator is attached to a facepiece and includes an inflow port for medium-pressure air ($S_1$), a supply port for the medium-pressure air ($S_1$) with respect to the facepiece, and a diaphragm. The supply valve includes a cylindrical housing and a slider that is reciprocally slidable on the inner peripheral surface of the housing in an axial direction thereof. The housing includes a pilot valve seat urged toward a pilot valve on an outer side of the one end portion in the axial direction and a main valve seat on an inner side of an opposite end portion in the axial direction. The inflow port is formed between the one end portion and the opposite end portion. The slider includes the pilot valve contactable with the pilot valve seat and a main valve urged toward the main valve seat.

10 Claims, 5 Drawing Sheets

SUPPLY VALVE FOR AIR RESPIRATOR

TECHNICAL FIELD

The present invention relates to supply valves suitably used for air respirators.

BACKGROUND

Air respirators used by firefighters and the like which are used with cylinders as air supply sources are conventionally known. Also, there are known high-pressure decompression valves which are used to decompress compressed air under high pressure in cylinders, and supply valves which are used to supply low-pressure air to the wearer of the air respirator by decompressing medium-pressure air obtained through the high-pressure decompression valve into pressure equivalent to atmospheric pressure. The supply valves are also referred to as air supply valves.

One example of the supply valves of this type is disclosed as pilot control two-stage regulator in JP 1983-501656 A (PTL 1). Regarding the regulator used as a scuba pilot regulator, when pressure in the mouth of the user of the air respirator is reduced, variation occurs in the diaphragm, and a linkage arm is moved according to the variation. When the linkage arm is moved, a lever is raised, whereby moving a pin along with the movement of a ball. The movement of the pin allows a pilot valve to open, and the medium-pressure air flows into a control room. A poppet valve is opened by the pressure of the medium-pressure air, and the air decompressed through the poppet valve is supplied to the mouth of the user.

CITATION LIST

Patent Literature

{PTL 1} JP 1983-501656 A

SUMMARY

Technical Problem

In the supply valve in which two valves such as the pilot valve and poppet valve are sequentially opened while supplying the air to the user of the air respirator, a considerable time is often required in a period during which the variation occurs in the diaphragm, and the poppet valve, which is a main valve, is left open.

An object of the present invention is to provide a supply valve improved to be capable of smoothly supplying air to a wearer of an air respirator when the internal pressure of the air respirator is reduced lower than setting pressure at which a diaphragm is activated.

Solution to Problem

Some embodiments of the present invention provide a supply valve for an air respirator configured to be attachable to a facepiece and to include an inflow port for medium-pressure air from a compressed air supply source, a supply port for the medium-pressure air to the facepiece, and a diaphragm to be activated when internal pressure of the facepiece being worn by the wearer is reduced lower than predetermined pressure, wherein the medium-pressure air is supplied to the facepiece via the supply port when the diaphragm is activated to leave the valve open.

The features of the supply valve for the air respirator according to the present invention are as follows. The supply valve for the air respirator may include a cylindrical housing and a slider configured to be reciprocally slidable on an inner peripheral surface of the housing in an axial direction of the housing. In the housing, a pilot valve seat is formed on an outer side of one end portion of opposite end portions in the axial direction, and the pilot valve seat is urged by a first spring in a direction directed from an outer side to an inner side of the housing and is coupled to the diaphragm provided on the outer side of the housing, and a main valve seat is formed on an inner side of an opposite end portion of the one end portion, and the inflow port is formed between the opposite end portions. In the slider, a pilot valve configured to be contactable with the pilot valve seat, and a main valve configured to be contactable with the main valve seat are formed, and the main valve is urged by a second spring in a direction that the main valve is contacted with the main valve seat. When a wearer of the facepiece is in a non-inhalation state, the supply valve of the facepiece under connection with the compressed air supply source is in a neutral state where the pilot valve is contacted with the pilot valve seat, and the main valve is contacted with the main valve seat. When the wearer is in an inhalation state, the diaphragm is activated in the facepiece, and the pilot valve seat moves in a direction against an urge of the first spring and is spaced away from the pilot valve, whereby leaving the pilot valve open. The medium-pressure air flowed in from the inflow port by leaving the pilot valve open allows the slider to slide in a direction against an urge of the second spring. The main valve is spaced away from the main valve seat by sliding the slider in the direction, whereby leaving the main valve open, and the medium-pressure air passes through between the main valve and the main valve seat and flows to the supply port, whereby flowing into the inside of the facepiece.

According to one embodiment of the present invention, in the housing, a pilot valve guide hole leading to an inside and an outside of the housing is formed at the one end portion, while the supply port is formed at the opposite end portion. The slider is configured to include at least three shaft portions that include a first shaft portion, a second shaft portion, and a third shaft portion, which are arranged in order from the one end portion to the opposite end portion of the housing. The first shaft portion is configured to be reciprocally slidable and hermetically engaged with the pilot valve guide hole in the axial direction and configured to include a part where the pilot valve is formed at a portion protruding from the pilot valve guide hole to the outside of the housing, and a part where a pilot chamber is defined between the first shaft portion and the inner peripheral surface of the housing, wherein a vent path opened to the outer side of the pilot valve and the pilot chamber is formed. The second shaft portion is configured to be reciprocally slidable and hermetically engaged with the inner peripheral surface of the housing in the axial direction and to include a guiding hole connecting to the inflow port and the pilot chamber. The third shaft portion is configured to define a medium-pressure air inflow portion connecting to the inflow port between the third shaft portion and the inner peripheral surface of the housing and configured to include the main valve to open and close the medium-pressure air inflow portion with respect to the supply port, wherein the main valve is spacably contacted with the main valve seat under the urge of the second spring when the supply valve is in the neutral state. A first lever extends from the diaphragm to the housing, and a rotatable second lever configured to include the pilot valve seat and configured to be urged by the first spring is provided on the outer side of the housing. The first lever and the second lever are configured to be coupled in such a manner that movements of the diaphragm are transmitted to the second lever via the first lever when the diaphragm is activated. When the internal pressure of the facepiece being worn by the wearer is reduced, and the diaphragm is activated, the second lever connected to the first lever rotates against the urge of the first spring, and the pilot valve seat is spaced away from the pilot valve, whereby leaving the pilot valve open. When the pilot valve is left open, air pressure of the pilot chamber is reduced, and the medium-pressure air flowing into the inflow port allows the slider to slide in a direction against the urge of the second spring, whereby allowing the main valve to be spaced away from the main valve seat and leaving the main valve open, and whereby allowing the medium-pressure air to flow into the inside of the facepiece.

According to another embodiment of the present invention, the pilot valve may be formed on one of the opposite end portions of the slider and the main valve may be formed on a remaining end portion of the slider.

According to even another embodiment of the present invention, the pilot valve and the main valve may simultaneously move in the axial direction of the housing.

According to yet another embodiment of the present invention, the housing and the slider may define the pilot chamber in the inside of the housing, and the pilot chamber may be an annular space whose axis corresponds with that of the first shaft portion.

According to still another embodiment of the present invention, the guiding hole connecting to the pilot chamber and the medium-pressure air inflow port may be formed in the slider.

According to a further embodiment of the present invention, regarding the pilot chamber, when the slider reciprocally slides in the axial direction, internal volume of the pilot chamber may be correspondingly decreased and increased.

According to an even further embodiment of the present invention, the first shaft portion and the third shaft portion may be formed smaller in diameter than the second shaft portion.

According to a yet further embodiment of the present invention, the second spring may be accommodated in the pilot chamber in such a manner as to go around the first shaft portion, and be a coil spring that stretches and contracts in the axial direction.

According to a still further embodiment of the present invention, a fourth shaft portion whose diameter is smaller than those of the second shaft portion and the third shaft portion may be formed between the second shaft portion and the third shaft portion in the slider.

Advantageous Effects of Invention

With respect to a supply valve according to the present invention, a pilot valve and a main valve are formed in a single slider, and when the slider slides in the inside of the housing by leaving the pilot valve open, the main valve is also left open. Accordingly, regarding the air respirator in which the supply valve is used, when the diaphragm is activated in response to the internal pressure of the facepiece, the medium-pressure air passes through the supply port and smoothly flows into the inside of the facepiece.

DESCRIPTION OF EMBODIMENTS

Figure 1:
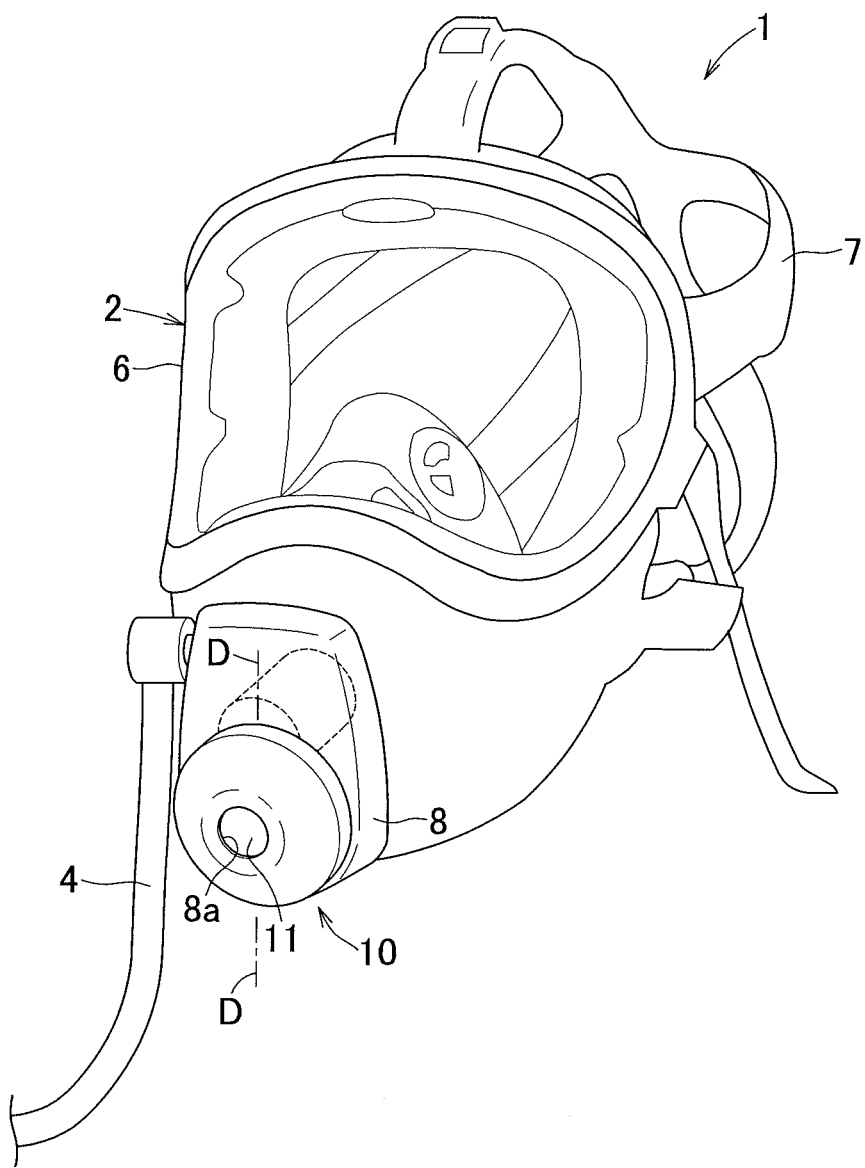
FIG. 1 is a perspective view of an air respirator.

Hereinafter, a supply valve according to the present invention will be described in detail by referring to the drawings.

FIG. 1 is a perspective view of an air respirator 1 in which a supply valve 10 is used. The air respirator 1 in the view is worn by a wearer, but the wearer is not shown in the view. The air respirator 1 includes a facepiece 2 through which inhalation and exhalation are performed, and an air supply hose 4 extended from the supply valve 10 attached on the facepiece 2, and the air supply hose 4 is connected to a high-pressure air cylinder (not shown) via a decompression valve and a stop valve (both not shown). The most part of the supply valve 10 is covered with a cover member 8 attached to the facepiece 2, and in the view, part of a diaphragm 11 and the air supply hose 4 of the supply valve 10 in the inside of an open hole 8a formed in the cover member 8 are visible. High-pressure air of the cylinder, which is normally set to about 30 MPa, is decompressed through the decompression valve to medium-pressure air $S_1$ (see FIG. 3) of about 0.7 to about 0.9 MPa, and passes through the supply valve 10 and advances to the inside of the facepiece 2 while being held under pressure corresponding to atmospheric pressure, which is used for inhalation for the wearer (not shown) of the facepiece 2. However, in the present invention, the medium-pressure air $S_1$ may also be referred to as the medium-pressure air $S_1$ even after the medium-pressure air $S_1$ has passed through the supply valve 10. Also, in FIG. 1, the exhalation of the wearer is discharged through a discharging check valve (not shown) provided in the facepiece 2. The facepiece 2 includes an eyepiece 6 and a head band 7 that are made of transparent plastic. Line D-D in FIG. 1 is a line that bisects the diaphragm 11 in the width direction of the facepiece 2.

Figure 2:
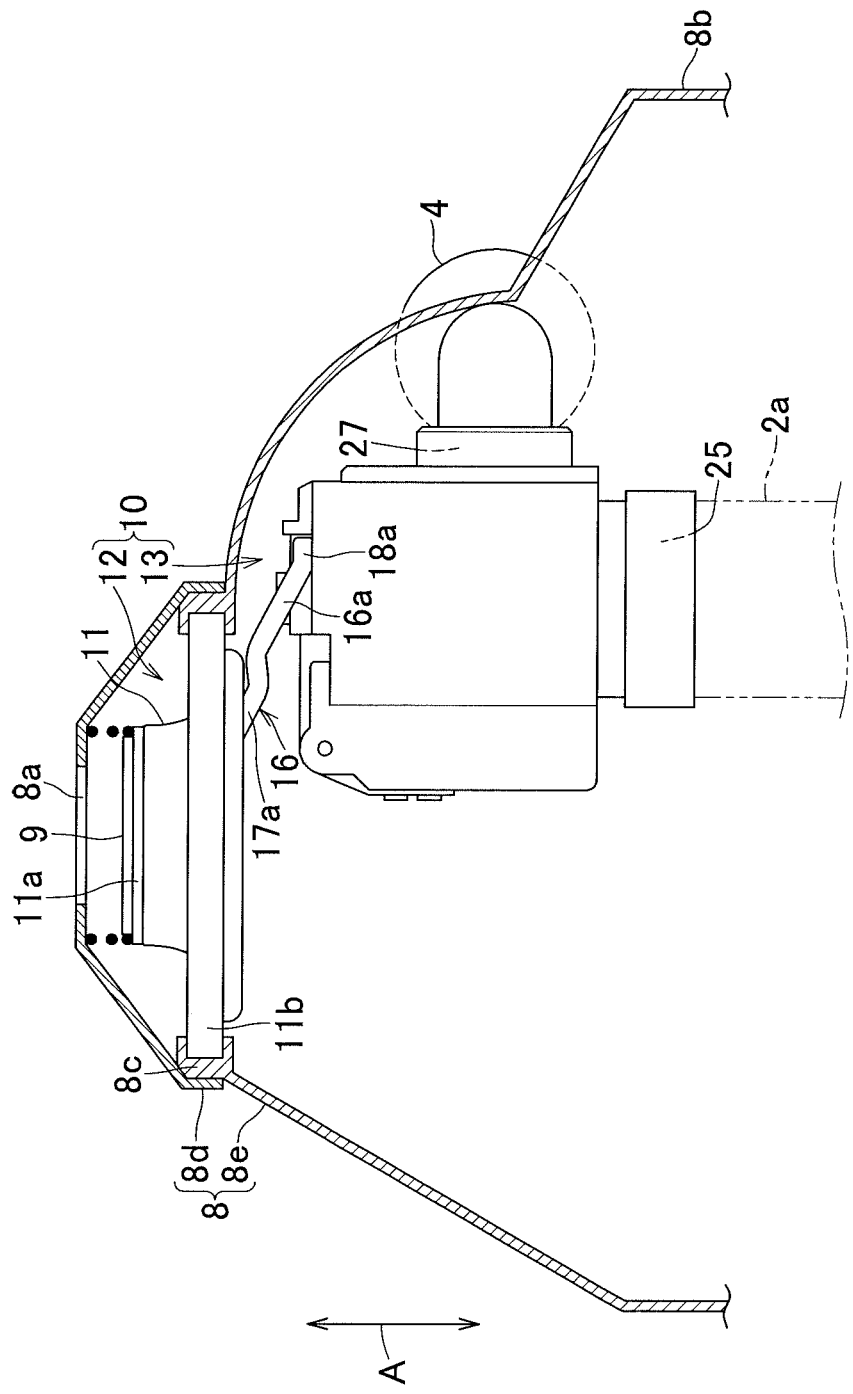
FIG. 2 is a diagram illustrating a side view of a supply valve used in the air respirator in FIG. 1.

FIG. 2 is a diagram illustrating a side face of the supply valve 10 fitted into the inside of the cover member 8 by the removal of the cover member 8 of FIG. 1. However, in FIG. 2, the direction of the supply valve 10 is varied in such a manner that an opening 8a of the cover member 8 and diaphragm 11 shown in FIG. 1 are positioned upwardly in the diagram, and an up-and-down direction in FIG. 2 is illustrated with a two-headed arrow A. The cover member 8 includes an anterior member 8d disposed in front of the diaphragm 11 (upper side in FIG. 2) and a posterior member 8e extending from the diaphragm 11 toward the facepiece 2, and a peripheral edge portion 8b of the posterior member 8e is hermetically attached to the facepiece 2. However, in order to simplify the description, the illustration of the facepiece 2 is omitted in FIG. 2. The supply valve 10 includes an actuator 12 in which an ordinary diaphragm 11 is used, and an air supply unit 13 whose body is separated from the actuator 12. The diaphragm 11 is formed in a conical trapezoid shape and includes a top portion 11a and a base portion 11b. The top portion 11a is pressed downwardly in the diagram by a positive-pressure spring 9 interposed between the top portion 11a and a peripheral edge portion of the opening 8a of the cover member 8. The base portion 11b is hermetically secured on a mounting portion 8c of the posterior member 8e. A first lever 16 extends from the diaphragm 11 to the air supply unit 13. In the air supply unit 13, the air supply hose 4 is coupled to a connecting port 27 (see FIG. 3) extending to a side direction in the diagram, and a vent pipe 2a connecting to the inside of the facepiece 2 is coupled to a medium-pressure air supply port 25 (see FIG. 3) downwardly extending in the diagram. However, in FIG. 2, the pipe 2a is illustrated in a imaginary line.

Figure 3:
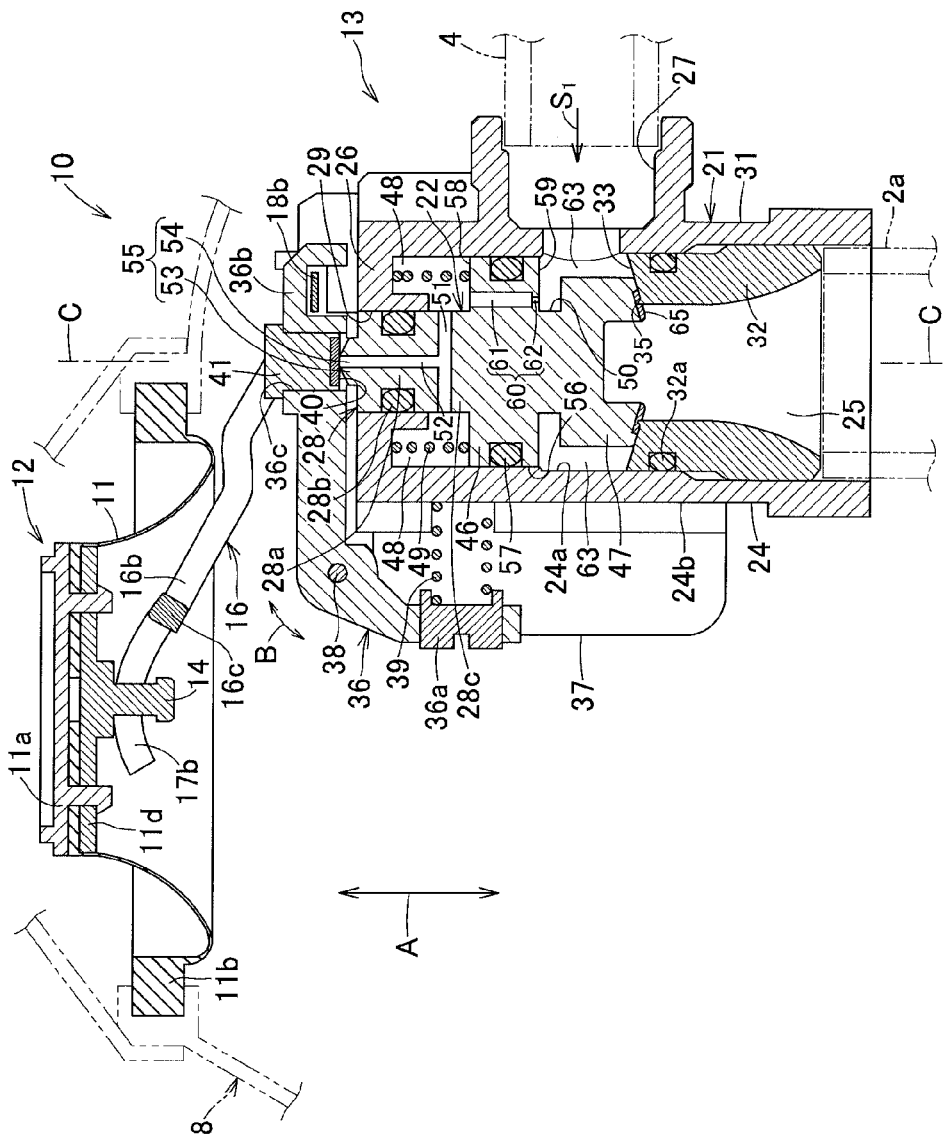
FIG. 3 is a diagram illustrating a cross section of the supply valve, which is similar to FIG. 2.

FIG. 3 is a diagram illustrating a cross section of the supply valve 10 of FIG. 2, and the cross section is obtained by cutting the supply valve 10 along the line D-D of FIG. 1. The supply valve 10 of FIGS. 2 and 3 is in a neutral state, and with regard to the supply valve 10 described above, a top plate 11d of the hollow diaphragm 11 formed in the conical trapezoid shape is attached to the top portion 11a, and a shaft portion 14 vertically hangs from the top plate 11d. The first lever 16 includes a pair of lever portions 16a and 16b that are parallelly spaced away from each other. In FIG. 2, one lever portion 16a out of the pair is illustrated, and in FIG. 3, the other lever portion 16b is illustrated. The shaft portion 14 of the diaphragm 11 is inserted between the pair of lever portions 16a and 16b. Also, a portion 16c shown in the lever portion 16b in FIG. 3 illustrates a cross section of a part connecting the pair of lever portions 16a and 16b. The lever portions 16a and 16b respectively includes upper end portions 17a and 17b and lower end portions 18a and 18b (collectively see FIG. 2), and the upper end portions 17a and 17b extend to the direction intersecting with the shaft portion 14 and come into contact with or slightly detach from the top plate 11d. The lower end portions 18a and 18b extend to the air supply unit 13.

Between the diaphragm 11 and the first lever 16 in FIG. 3, as described above, the diaphragm 11 is such that the top portion 11a and the top plate 11d integrally attached to the top portion 11a can descend and ascend in the up-and-down direction A. For example, when the internal pressure of the facepiece 2 is reduced lower than a predetermined value, the top plate 11d of the diaphragm descends in accordance with the reduced internal pressure while downwardly pressing the upper end portions 17a and 17b of the first lever 16.

The air supply unit 13 includes a cylindrical housing 21 and a slider 22 that is accommodated in the housing 21 and is slidable in the up-and-down direction A with respect to an inner peripheral surface 24a of a peripheral wall 24 of the housing 21. In FIG. 3, a center line C-C that bisects the internal diameter of the housing 21 is also illustrated.

The housing 21 is made up of the peripheral wall 24 and a top wall 26, and a connecting port 27 to which an end portion of the air supply hose 4 is detachable, and a medium-pressure air supply port 25 to which the vent pipe 2a extending from the facepiece 2 is detachable are formed on the peripheral wall 24. The connecting port 27 serves as an inflow port of the medium-pressure air $S_1$ in the supply valve 10. A top-portion through-hole 29, which is used as a guide hole for a pilot valve, is formed on the top wall 26. In the top-portion through-hole 29, an upward portion 28a including a pilot valve 55 described later and formed at a first shaft portion 28 of the slider 22 is slidably inserted in the up-and-down direction A. An O-ring 28b which is hermetically attached to a peripheral surface of the through-hole 29 is attached to the upper portion 28a. A lower end portion 31 of the housing 21 is left open toward the inside of the facepiece 2 via the vent pipe 2a attached to the medium-pressure air supply port 25. An annular member 32 is inserted in the inside of the lower end portion 31, and a space between the annular member 32 and the inner peripheral surface 24a of the peripheral wall 24 is hermetically sealed with an O-ring 32a attached to the annular member 32. The annular member 32 includes an annular top surface 33 extending to the inner peripheral surface 24a, and the top surface 33 has a falling gradient from the inner peripheral surface 24a to the center axis C of the housing 21. Also, the top surface 33 includes a main valve seat 35 formed on a flat surface going around the inner peripheral surface 24a. It is noted that it is possible to change the shape of the supply valve 10 in such a manner that the top surface 33 has a rising gradient toward the center axis C.

A pilot lever 36, which is referred to as a second lever according to the present invention, is attached to the outer peripheral surface 24b of the peripheral wall 24 of the housing 21 via a plate portion 37. The plate portion 37 is secured on the outer peripheral surface 24b, and the pilot lever 36 is attached rotatably clockwise and counterclockwise, which is shown in a two-headed arrow B, centering on a shaft portion 38 provided in the plate portion 37, and is urged clockwise in the diagram by a first spring 39 that serves as an urging means interposed between the lower end portion 36a of the pilot lever 36 and the outer peripheral surface 24b of the peripheral wall 24. At the upper end portion 36b of the pilot lever 36, a block 41 formed of a non-elastic member such as metal and rigid plastic is press-fitted into a through-hole 36c formed on the upper end portion 36b. A part of the lower surface of the block 41 is a pilot valve seat 40, and the pilot valve seat 40 is formed of an elastic member such as synthetic rubber. The upper end portion 36b is also contacted with or is positioned to be contactable with the lower end portions 18a and 18b of the first lever 16 extending from the actuator 12 from below in the up-and-down direction A.

The slider 22 includes at least three shaft portions including the first shaft portion 28, a second shaft portion 46, and a third shaft portion 47, which are arranged from the upward direction to the downward direction in FIG. 3. In the diagram illustrated in FIG. 3, a fourth shaft portion 50 whose diameter is smaller than those of both shaft portions 46 and 47 is also formed between the second shaft portion 46 and the third shaft portion 47.

In addition to the upper portion 28a, the first shaft portion 28 includes a lower portion 28c, formed in a cylindrical shape, whose diameter is equal to that of the upper portion 28a. The lower portion 28c is spaced away from the inner peripheral surface 24a of the peripheral wall 24, whereby defining a pilot chamber 48 between the inner peripheral surface 24a and the lower portion 28c. The pilot chamber 48 is also defined by the housing 21 and the slider 22, which can be said as an annular space in which the first shaft portion 28 is positioned as a shaft. In the pilot chamber 48, a coiled second spring 49, which is an urging means, is accommodated in such a manner as to go round the first shaft portion 28. In the first shaft portion 28, a first vent path 51 is formed that penetrates the first shaft portion 28 in the radial direction, wherein both ends thereof are opened to the pilot chamber 48, and a second vent path 52 is formed which extends from the first vent path 51 along the center line C and includes an opening 54 at a top portion 53 of the first shaft portion 28. The top portion 53 including the opening 54 forms the pilot valve 55 spacably contacted with the pilot valve seat 40, and in the diagram, the pilot valve 55 and the pilot valve seat 40 are hermetically contacted.

The second shaft portion 46 is slidably and hermetically contacted with the inner peripheral surface 24a of the peripheral wall 24 via an O-ring 57 attached on the outer peripheral surface 56 thereof. The second shaft portion 46 also includes an annular upper surface 58 and an annular lower surface 59, and a guiding hole 60 is formed between the upper surface 58 and the lower surface 59. The guiding hole 60 includes an upper portion 61, which is open on the upper surface 58, whose internal diameter is large, and a lower portion 62, which is open on the lower surface 59, whose internal diameter is small. The lower surface 59 is positioned upwardly with respect to the connecting port 27 formed on the peripheral wall 24. Incidentally, as one example of the guiding hole 60, which is desirable for the supply valve 10 used in the air respirator 1, the upper portion 61 has a diameter equal to or larger than 0.8 mm, and the lower portion 62 has a diameter equal to or smaller than 0.2 mm.

The third shaft portion 47 is spaced away from the inner peripheral surface 24a of the peripheral wall 24, whereby defining a medium-pressure air inflow portion 63 as a gap between the third shaft portion 47 and the inner peripheral surface 24a. A lower end of the third shaft portion 47 includes a main valve 65 which is spacably and hermetically contacted with the main valve seat 35 in the housing 21. The main valve 65 in the diagram illustrated is formed of an elastic member such as synthetic rubber, and the main valve seat 35 is formed of non-elastic members such as metal and rigid plastic. However, in the present invention, the non-elastic member may be applied to the main valve 65, and the elastic member may be applied to the main valve seat 35. When the top surface 33 of the annular member 32 on which the main valve seat 35 is formed has a rising gradient toward the center axis C, it may be such that the shape of the main valve 65 can be varied so as to have a rising gradient toward the center axis C.

The fourth shaft portion 50 is formed whose diameter is smaller than those of the second shaft portion 46 and the third shaft portion 47. As a result, effects are obtained that the slider 22 can form the guiding hole 60 in the second shaft portion 46 without increasing the diameter of the second shaft portion 46. However, when the effects are not necessary, the third shaft portion 47 can be formed immediately below the second shaft portion 46 by omitting the fourth shaft portion 50.

In the air supply unit 13 being in a neutral state in FIG. 3, a coiled second spring 49 accommodated in the pilot chamber 48 is in an urged state, wherein the spring 49 is press-contacted with the top wall 26 of the housing 21 and the upper surface 58 of the second shaft portion 46 of the slider 22 and downwardly presses the slider 22 to the housing 21 and allows the main valve 65 formed in the third shaft portion 47 and the main valve seat 35 formed in the housing 21 to be attached. This adhesion state is made as follows. That is, the medium-pressure air $S_1$ is supplied from the air supply hose 4 to the medium-pressure air inflow portion 63 formed in the inside of the housing 21, and the medium-pressure air $S_1$ passes through the guiding hole 60 formed in the second shaft portion 46 and enters the pilot chamber 48. Accordingly, air pressure is equivalent between the pilot chamber 48 and the medium-pressure air inflow portion 63, and the slider 22 is downwardly urged by action of the second spring 49, whereby the main valve 65 is hermetically attached to the main valve seat 35. In FIG. 3, the pilot valve 55 formed in the first shaft portion 28 of the slider 22 is also hermetically attached to the pilot valve seat 40 formed on the pilot lever 36 that is disposed under the influence of the urge of the first spring 39.

Figure 4:
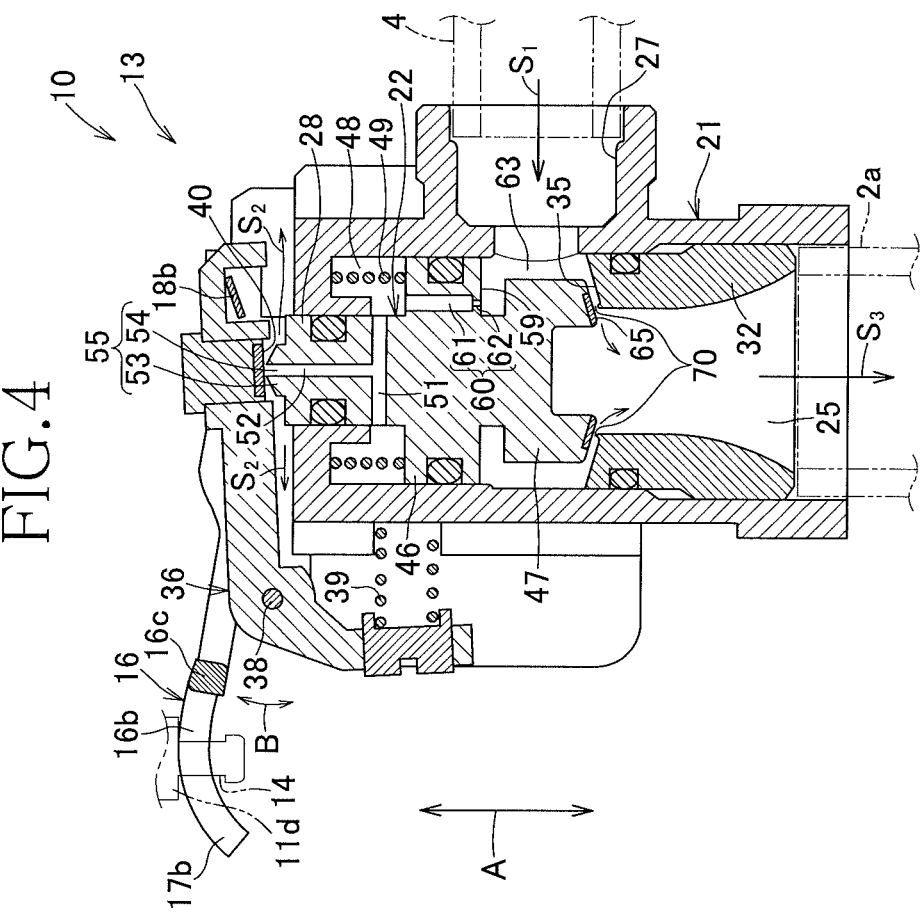
FIG. 4 is a diagram illustrating the supply valve in an air supply state, which is similar to FIG. 3.

FIG. 4 is a diagram, which is similar to FIG. 3, illustrating a state where the wearer (not shown) of the facepiece 2 exhales during breathing operation, and an air-supply state where the supply valve 10 supplies the medium-pressure air $S_1$ to the facepiece 2. However, in FIG. 4, the diaphragm 11 is not shown in the diagram, and only part of the top plate 11d and the shaft portion 14 are illustrated in an imaginary line. When the facepiece 2 of FIG. 3 is worn by the wearer, and the internal pressure of the facepiece 2 starts being reduced, and the internal pressure reaches predetermined pressure at which the diaphragm 11 starts acting, the top plate 11d of the diaphragm 11 descends while pushing down the upper end portions 17a and 17b of the first lever 16. Then, the lower end portions 18a and 18b of the first lever 16 ascend, whereby rotating the pilot lever 36 counterclockwise shown in the two-headed arrow B in the diagram against the urge of the first spring 39. Subsequently, the pilot valve seat 40 formed in the pilot lever 36 is spaced away from the pilot valve 55 formed in the slider 22, whereby leaving the pilot valve 55 open and leaving the first vent path 51 and the second vent path 52 of the slider 22 open toward the inside of the facepiece 2.

When the pilot valve 55 is left open, the medium-pressure air $S_1$ held in the pilot chamber 48 passes through the first vent path 51 and the second vent path 52 and is turned into air $S_2$ which advances to the inside of the facepiece 2, whereby air pressure in the pilot chamber 48 is reduced. In contrast, the medium-pressure air $S_1$ flows from the connecting port 27 into the medium-pressure air inflow portion 63 of the housing 21. The medium-pressure air $S_1$ is likely to pass through the guiding hole 60 connecting the pilot chamber 48 with the medium-pressure air inflow portion 63 and enter the pilot chamber 48. However, the guiding hole 60 includes a lower portion 62 whose internal diameter is small, and that works in such a manner as to suppress the approach speed of the medium-pressure air $S_1$ into the pilot chamber 48. Accordingly, in the air supply unit 13 in FIG. 4, while the pilot chamber 48 is left open, and its internal air pressure is reduced, the pressure of the medium-pressure air $S_1$ works on the lower surface 59 of the second shaft portion 46, and a difference between the pressure of the second spring 49 that works on the slider 22 to descend and the pressure of the medium-pressure air $S_1$ that works on the slider 22 to ascend allows the slider 22 to upwardly move in the up-and-down direction A. In the slider 22 moving upwardly, the main valve 65 is spaced away from the main valve seat 35, whereby forming a gap 70, which is ventilated, between the main valve 65 and the main valve seat 35. Then, the medium-pressure air $S_1$ supplied from the air supply hose 4 passes through the medium-pressure air inflow portion 63 and the gap 70 and enters the inside of the annular member 32 and further passes through the supply port 25 and is turned into a low-pressure air $S_3$ for inhalation, which enters the inside of the facepiece 2.

When the inhalation operation of the wearer stops, that is, when the breathing operation becomes a non-inhalation state, the internal pressure of the facepiece 2 is gradually increased by the air $S_3$ to be flowed in, and the diaphragm 11 that has descended ascends, moves to a direction of returning to the state shown in FIG. 3, and moves to a direction that the pilot valve seat 40 closes the pilot valve 55. Also, in the inside of the housing 21, the medium-pressure air $S_1$ passes through the guiding hole 60 and enters the pilot chamber 48, whereby equalizing the air pressure of the pilot chamber 48 with the air pressure of the medium-pressure air inflow portion 63. As a result, a state shown in FIG. 3 is returned where the action of the second spring 49 allows the slider 22 to move downwardly, and the main valve 65 and the main valve seat 35 are attached, whereby preventing the medium-pressure air $S_1$ from passing through the supply port 25 and entering the facepiece 2. The internal volume of the pilot chamber 48 decreases and increases in accordance with the sliding movement of the slider 22 in the up-and-down direction A.

Figure 5:
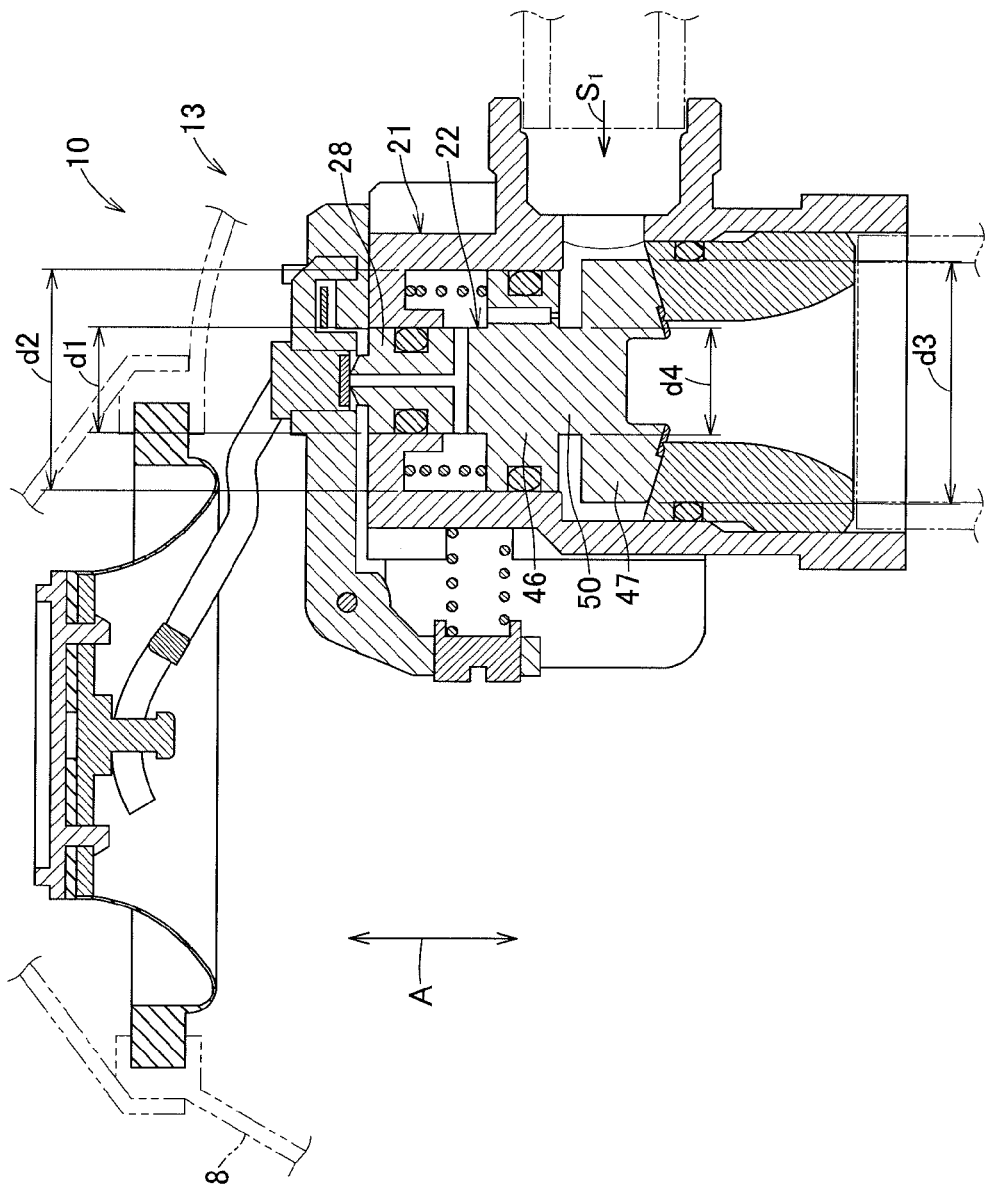
FIG. 5 is a diagram illustrating a mode of the supply valve, which is similar to FIG. 3.

FIG. 5 is a diagram, which is similar to FIG. 3, illustrating an embodiment of the supply valve 10. The supply valve 10 in FIG. 5 includes the housing 21 and the slider 22, and the first shaft portion 28, the second shaft portion 46, and the third shaft portion 47, and the fourth shaft portion 50 are formed in the slider 22. However, this slider 22 is formed such that the diameter d1 of the first shaft portion 28 is smaller than the diameter d2 of the second shaft portion 46, and the diameter d2 of the second shaft portion 46 is smaller than the diameter d3 of the third shaft portion 47, and the diameter d4 of the fourth shaft portion 50 is smaller than the diameter d2 of the second shaft portion 46 and the diameter d3 of the third shaft portion 47.

The supply valve 10 according to the present invention uses the pilot valve 55 and the main valve 65, and the pilot valve 55 is formed on one of opposite end portions of the slider 22 and the main valve 65 is formed on a remaining other end portion of the slider 22 in the sliding direction. When the pilot valve 55 is left open, and the slider 22 moves upwardly in the up-and-down direction A, the main valve 65 also moves upwardly, which allows the main valve 65 to smoothly be opened. Accordingly, with regard to the air respirator 1 in which the supply valve 10 is used, when the internal pressure of the facepiece 2 becomes lower than predetermined pressure, the supply of air for inhalation to the facepiece 2 as a response to the internal pressure is smoothly carried out, that is, the supply of air for inhalation to the facepiece 1 is not delayed, so that the wearer of the air respirator 1 can readily breathe.

Also, with regard to the supply valve 10, in the case where the slider 22 is smoothly moved, the area of the upper surface 58 or the lower surface 59 of the second shaft portion 46 only needs to be increased. In other words, when the area of the upper surface 58 or the lower surface 59 is increased, it needs not necessarily to increase the internal volume of the housing 21, whereby making it easy to miniaturize the supply valve 10.

Also, when the slider 22 slides upwardly, the main valve 65 of the supply valve 10 is definitely left open, so that the sliding distance of the slider 22 can be shortened regarding the supply valve 10, whereby making it easy to miniaturize the supply valve 10.

The main valve 65 described above is formed as part of the slider 22 formed of non-elastic members such as metal and rigid plastic. In contrast, with regard to the conventional technology in which the main valve is formed of only elastic sheets such as rubber sheets, when the main valve is required to readily be left open, the diameter of the valve needs to be increased. As a result, the supply valve is often increased in size. Compared with the conventional technology, the supply valve 10 according to the present invention is not required to increase the diameter of the main valve as described in the conventional technology, which readily facilitates miniaturization in that sense.

The pilot chamber 48 of the supply valve 10 according to the present invention can be designed without being limited by the size of the main valve 65, and the main valve 65 can be designed without being limited by the diameter of the second shaft portion 46.

REFERENCE SIGNS LIST 1 air respirator
2 facepiece
10 supply valve
11 diaphragm
16 first lever
22 slider
25 supply port
27 inflow port (connecting port)
28 first shaft portion
29 guide hole for pilot valve (top-portion through-hole, through-hole)
35 main valve seat
36 second lever (pilot lever)
39 first spring
46 second shaft portion
47 third shaft portion
48 pilot chamber
49 second spring
50 fourth shaft portion
55 pilot valve
60 guiding hole
63 medium-pressure air inflow portion
65 main valve
$S_1$ medium-pressure air

The invention claimed is:

1. A supply valve for an air respirator configured to be attachable to a facepiece, the supply valve comprising:
    an inflow port for medium-pressure air from a compressed air supply source;
    a supply port for the medium-pressure air to the facepiece; and
    a diaphragm to be activated when internal pressure of the facepiece being worn by the wearer is reduced lower than predetermined pressure, wherein
    the medium-pressure air is supplied to the facepiece via the supply port when the diaphragm is activated to leave the valve open, wherein:
    the supply valve for the air respirator further comprises a cylindrical housing and a slider configured to be reciprocally slidable on an inner peripheral surface of the housing in an axial direction of the housing;
    in the housing, a pilot valve seat is formed on an outer side of one end portion of opposite end portions in the axial direction, and the pilot valve seat is urged by a first spring in a direction directed from an outer side to an inner side of the housing and is coupled to the diaphragm provided on the outer side of the housing, and a main valve seat is formed on an inner side of an opposite end portion of the one end portion, and the inflow port is formed between the opposite end portions;
    a pilot valve contactable with the pilot valve seat, and a main valve configured to be contactable with the main valve seat are formed in the slider, and the main valve is urged by a second spring in a direction that the main valve is contacted with the main valve seat;
    when a wearer of the facepiece is in a non-inhalation state, the supply valve of the facepiece under connection with the compressed air supply source is in a neutral state where the pilot valve is contacted with the pilot valve seat, and the main valve is contacted with the main valve seat; and
    when the wearer is in an inhalation state, the diaphragm is activated in the facepiece, and the pilot valve seat moves in a direction against an urge of the first spring and is spaced away from the pilot valve contacted, whereby leaving the pilot valve open, and the medium-pressure air flowed in from the inflow port by leaving the pilot valve open allows the slider to slide in a direction against an urge of the second spring, and the main valve is spaced away from the main valve seat by sliding the slider in the direction, whereby leaving the main valve open, and the medium-pressure air passes through between the main valve and the main valve seat and flows to the supply port, whereby flowing into the inside of the facepiece.

2. The supply valve according to claim 1, wherein,
    in the housing, a pilot valve guide hole leading to an inside and an outside of the housing is formed at the one end portion, while the supply port is formed at the opposite end portion;
    the slider is configured to include at least three shaft portions that include a first shaft portion, a second shaft portion, and a third shaft portion, which are arranged in order from the one end portion to the opposite end portion of the housing;

the first shaft portion is configured to be reciprocally slidable and hermetically engaged with the pilot valve guide hole in the axial direction and configured to include a part where the pilot valve is formed at a portion protruding from the pilot valve guide hole to the outside of the housing, and a part where a pilot chamber is defined between the first shaft portion and the inner peripheral surface of the housing, wherein a vent path opened to the outer side of the pilot valve and the pilot chamber is formed;

the second shaft portion is configured to be reciprocally slidable and hermetically engaged with the inner peripheral surface of the housing in the axial direction and configured to include a guiding hole connecting to the inflow port and the pilot chamber;

the third shaft portion is configured to define a medium-pressure air inflow portion connecting to the inflow port between the third shaft portion and the inner peripheral surface of the housing and configured to include the main valve to open and close the medium-pressure air inflow portion with respect to the supply port, wherein the main valve is spacably contacted with the main valve seat under the urge of the second spring when the supply valve is in the neutral state;

a first lever extends from the diaphragm to the housing, and a rotatable second lever configured to include the pilot valve seat and configured to be urged by the first spring is provided on the outer side of the housing, and the first lever and the second lever are configured to be coupled in such a manner that movements of the diaphragm are transmitted to the second lever via the first lever when the diaphragm is activated; and when the internal pressure of the facepiece is reduced, and the diaphragm is activated, the second lever connected to the first lever rotates against the urge of the first spring, and the pilot valve seat is spaced away from the pilot valve, whereby leaving the pilot valve open, and when the pilot valve is left open, air pressure of the pilot chamber is reduced, and the medium-pressure air flowing into the inflow port allows the slider to slide in a direction against the urge of the second spring, whereby allowing the main valve to be spaced away from the main valve seat and leaving the main valve open, and whereby allowing the medium-pressure air to flow into the inside of the facepiece.

3. The supply valve according to claim 1, wherein the pilot valve is formed on one of the opposite end portions of the slider and the main valve is formed on a remaining end portion of the slider.

4. The supply valve according to claim 1, wherein the pilot valve and the main valve simultaneously move in the axial direction of the housing.

5. The supply valve according to claim 2, wherein the housing and the slider define the pilot chamber in the inside of the housing, and the pilot chamber is an annular space whose axis corresponds with that of the first shaft portion.

6. The supply valve according to claim 2, wherein the guiding hole connecting to the pilot chamber and the medium-pressure air inflow port is formed in the slider.

7. The supply valve according to claim 2, wherein, regarding the pilot chamber, when the slider reciprocally slides in the axial direction, internal volume of the pilot chamber is correspondingly decreased and increased.

8. The supply valve according to claim 2, wherein the first shaft portion and the third shaft portion are formed smaller in diameter than the second shaft portion.

9. The supply valve according to claim 2, wherein the second spring is accommodated in the pilot chamber in such a manner as to go around the first shaft portion, and is a coil spring that stretches and contracts in the axial direction.

10. The supply valve according to claim 2, wherein a fourth shaft portion whose diameter is smaller than those of the second shaft portion and the third shaft portion is formed between the second shaft portion and the third shaft portion in the slider.

* * * * *